United States Patent
Pastyr et al.

(10) Patent No.: US 6,730,924 B1
(45) Date of Patent: May 4, 2004

(54) COLLIMATOR FOR LIMITING A BUNDLE OF HIGH-ENERGY RAYS

(75) Inventors: Otto Pastyr, Leimen (DE); Gernot Echner, Wiesenbach (DE); Wolfgang Schlegel, Heidelberg (DE); Walter Ganter, Walldorf (DE)

(73) Assignee: Deutsches Krebsforschungszentrum Stiftung Des Oeffentlichen Rechts, Heidelberg (DE)

( * ) Notice: Subject to any disclaimer, the term of this patent is extended or adjusted under 35 U.S.C. 154(b) by 0 days.

(21) Appl. No.: 09/890,218

(22) PCT Filed: Jan. 12, 2000

(86) PCT No.: PCT/EP00/00153

§ 371 (c)(1),
(2), (4) Date: Jul. 26, 2001

(87) PCT Pub. No.: WO00/48203

PCT Pub. Date: Aug. 17, 2000

(30) Foreign Application Priority Data

Feb. 12, 1999 (DE) .......................................... 199 05 823

(51) Int. Cl.[7] .................................................. G21K 1/02
(52) U.S. Cl. ...................... 250/505.1; 378/150; 378/152
(58) Field of Search ........................ 250/505.1; 378/147, 378/150, 152, 153, 151

(56) References Cited

U.S. PATENT DOCUMENTS

| | | | |
|---|---|---|---|
| 3,151,245 | A | 9/1964 | Wilson |
| 4,987,309 | A | 1/1991 | Klasen |
| 5,144,647 | A | 9/1992 | Kikuchi |
| 5,166,531 | A | 11/1992 | Huntzinger |
| 5,724,400 | A | * 3/1998 | Swerdloff et al. ............ 378/65 |

FOREIGN PATENT DOCUMENTS

| | | |
|---|---|---|
| DE | 33 11 870 | 10/1983 |
| DE | 36 16 141 | 11/1987 |
| DE | 37 11 245 | 10/1988 |
| DE | 195 04 054 | 8/1998 |
| EP | 0 193 509 | 9/1986 |
| EP | 0 245 768 | 11/1987 |
| EP | 0 259 989 | 3/1988 |
| EP | 0 286 858 | 10/1988 |
| EP | 0 314 214 | 5/1989 |
| EP | 0 387 921 | 9/1990 |
| EP | 0 556 874 | 8/1993 |
| EP | 0 562 644 | 9/1993 |
| FR | 2 519 465 | 7/1983 |

OTHER PUBLICATIONS

Motorized Micro Multileaf Collimator Brochure 90/16505, Leibinger, Freiburg, Germany, Jun. 1998.

* cited by examiner

*Primary Examiner*—Kiet T. Nguyen
(74) *Attorney, Agent, or Firm*—Paul Vincent

(57) ABSTRACT

The invention relates to a collimator (1) for limiting a bundle of high-energy rays (2), which is emitted by a substantially point-like radiation source (3) and directed towards a treatment object (20) and used in particular for the stereotactic conformation radiotherapy of tumors. According to the invention the collimator (1) comprises a plurality of diaphragm leaves (4, 4') which are arranged opposite each other and which are made of a radiation-absorbing material and which, by means of drive mechanisms, can be moved into the optical path in such a way that the contours and/or exposure period of said optical path can be freely defined, the front edges (5, 5') of the diaphragm leaves (4, 4') being parallel to the optical path at all times. Avoiding penumbral shadows with this kind of collimator (1) is made considerably easier if the diaphragm leaves (4, 4') consists of a rear partial element (6, 6') which can be linearly displaced and a front partial element (7, 7') which is hinged to same. Drive means adjust the front partial element (7, 7') in accordance with the prevailing position of the rear partial element (6, 6') in such a way that the front edges (5, 5') are parallel to the optical path at all times.

32 Claims, 8 Drawing Sheets

COLLIMATOR FOR LIMITING A BUNDLE OF HIGH-ENERGY RAYS

BACKGROUND OF THE INVENTION

The invention concerns a multiple leaf collimator for limiting a bundle of high-energy rays emitted by a substantially point-like radiation source and directed towards a treatment object and used in particular for the stereotactic conformation radiotherapy of tumors, wherein the collimator contains a plurality of opposing collimator leaves made of a radiation-absorbing material which can be moved by drive mechanisms into the optical path such that the contours of said optical path can be freely defined, wherein the front edges of the collimator leaves are always aligned in parallel to the optical path.

The treatment devices used today in oncological radiation therapy are provided with collimators which limit high-energy radiation, in most cases high-energy gamma radiation from a linear accelerator, in such a fashion that the rays assume exactly the same shape as the object to be treated. Since irradiation e.g. of a tumor, is implemented from different directions, a high irradiation intensity on the tumor can be effected with only limited exposure to the surrounding tissue. For absorbing high-energy radiation, the collimator must have a thickness of several centimeters, which produces a half shadow when the passage opening has straight walls in the passage direction. Since the rays diverge from the substantially point-like radiation source, the collimator opening is smaller than the actual shape of the tumor so that the collimated rays diverge to have exactly the size of the tumor upon impingement. When the walls of the collimator opening are straight, part of the radiation will not be shielded by the full material thickness due to the inclined path of the radiation. In consequence thereof, either healthy tissue surrounding the tumor is exposed to considerable radiation or the tumor tissue will receive too little dosage. This causes damage which should be prevented. For this reason, one of average skill in the art has tried to develop different collimators which reduce or prevent these half shadows.

One suggestion to prevent half shadows which has been described in the literature, consists in providing the collimator leaves (leaves) of a collimator (multi-leaf collimator) with an irregular trapezoidal shape such that their side surfaces and the side surfaces of the outer limits of the collimator opening have the angle of the optical path. It is, however, more difficult to achieve corresponding alignment of the front edges of the collimator leaves. Many suggestions have been made to solve this problem, none of which is satisfying.

In one suggestion made e.g. in EP 0 259 989 B1, EP 0 556 874 B1, EP 0 562 644 B1, U.S. Pat. No. 5,166,531 and DE 33 11 870 C2, the front edges of the collimator leaves have a rounded shape such that the outer rays of the bundle contact these front edges tangentially. Through this solution, the half shadow can be weakened but not prevented. The same is true for a further suggestion made in EP 0 259 989 B1, EP 0 556 874 B1 and EP 0 562 644 B1, wherein the radiation must pass two sequential collimator openings. In DE 195 04 054 A1, such graduation of the front edges of the collimator leaves was further refined by constructing each collimator leaf from a plurality of rods, disposed one on top of the other such that they can be displaced with respect to one another. This collimator is complicated due to the large number of parts and exhibits increased radiation leakage due to the bordering of many collimator leaf elements and the associated unavoidable tolerances. Moreover, no drive mechanism is provided. Adjustments must be made by hand and automatic computer-controlled adjustment of the collimator opening is not possible.

DE 33 11 870 C2, U.S. Pat. No. 3,151,245, U.S. Pat. No. 4,987,309, U.S. Pat. No. 5,144,647, EP 0 193 509, EP 0 245 768 B1, the substantially idendical EP 0 387 921, and EP 0 314 214 B1 proposed moving the collimator leaves along curved paths such that the front edges of the collimator leaves are always aligned parallel to the optical path. This requires complicated guidance of the collimator leaves. The arrangement of such complicated guidance means imposes limits on the goal of minimizing the thickness of the collimator leaves. Collimator leaves must be thin to exactly reproduce the shape of the tumor, since rough graduations result in healthy tissue also being irradiated and destroyed or badly damaged. Moreover, if the collimator leaves have the shape of irregular trapezoids and are guided on curved paths, jamming can occur in consequence of this geometrical shape. To prevent same, DE 37 11 245 A1 proposes tapering the collimator leaves towards their front end facing the optical path. Wide opening of a collimator of this type produces gaps which cause increased leakage of rays. Finally, the problems of EP 0 314 213 B1 and U.S. Pat. No. 4,987,309 were believed to be solved by disposing the trapezoidal collimator leaves and the collimator leaves which can be displaced on curved paths such that the bundle of rays must pass through both collimator openings. Although each of the two collimators has a half shadow which is reduced by the other respective collimator, half shadows can only be eliminated with twice the shielding, i.e. almost twice as much material thickness is required. The amount of effort needed for drive and control is also doubled.

In addition, collimators have been disclosed (FR A 2519 465 and EP A 0286 858) which are composed of two pairs of shielding blocks offset from each other by 90°. These shielding blocks have front and rear components for preventing half shadows, wherein the latter can be aligned parallel to the optical path. The front blocks have sidewardly projecting bearing pins for pivoting on a holding device which is also connected to the rear blocks and on which drive means act for adjustment. These collimators can, however, only define a rectangular beam and a shape in the form of an object which is to be treated within a living organism, such as a tumor, can not be generated. This requires a shaping multiple leaf collimator of the above mentioned kind. The technical solution cannot easily be transferred to a multiple leaf collimator since a sideward bearing of forward components of this type cannot be effected with leaves of a multiple leaf configuration at those locations at which an adjacent leaf must be disposed for forming the above mentioned shape. A strict requirement for multiple leaf collimators is the absence of any shielding gaps between the leaves forming the shape since the associated leakage would destroy healthy tissue.

It is therefore the underlying purpose of the invention to solve the above-mentioned problems and to produce a multiple leaf collimator which eliminates half shadows with as little effort as possible.

SUMMARY OF THE INVENTION

This object is achieved in accordance with the invention in that the collimator leaves consist of a rear part which can be displaced linearly, and a front part connected thereto, wherein the front part of each collimating leaf is adjusted in correspondence with the respective position of the associated rear part through drive means such that the front edges are always aligned parallel to the optical path and such that the connection between the front part and the rear part does not lead to any significant gaps in the volume of the radiation absorbing material.

The present invention omits complicated curved displacement of the collimator leaves to simplify mechanics and reduce leaking radiation, since the linear displacement permits closer tolerances. From the point of view of mechanics and drive technology, adjustment of the front part can be realized in a considerably better and easier fashion compared to the curved displacement of prior art. The complete surface of the full material thickness is used for shielding to completely eliminate half shadows without requiring either the increased effort or additional shielding of the above-mentioned prior art. The suggested technical solution is superior with respect to the previous approaches, in particular when the collimator leaves have a trapezoidal shape to also prevent the half shadow caused by the side surfaces of the collimator leaves. The linear guidance avoids jamming even when the collimator leaves are trapezoidal which permits closer tolerances and reduction of leakage compared to collimator leaves with curved guidance. Only the front parts require a somewhat increased tolerance to prevent interference during adjustment in consequence of the trapezoidal shape. This tolerance is minimal compared to that of a curved guidance system. It is clear that the invention is not limited to trapezoidal collimator leaves in dependence on the size of the collimator and the angle of the optical path.

The invention provides that the front part is pivoted on the rear part, such that the volume of the ray-absorbing material is substantially uninterrupted. This should be taken into consideration in the concrete embodiment of pivoting, wherein there are several possibilities which will be explained below.

It is possible to provide separate drives for displacing the rear parts of the collimator leaves and for adjustment of the front parts, respectively, wherein these are matched by computer control. The drive means are preferably designed such that forced mechanical coupling into each position of the rear part guarantees the associated alignment of the front part and thereby the front edges, to prevent misalignment of the front edges in consequence of program or drive means error. The reliability is considerably increased, which is particularly important for patients and users. Further advantages of this embodiment consist in that only one drive is required for each collimator leaf which requires correspondingly less computer work to thereby obtain more rapid calculation results and faster adjustment of the collimator to another shape.

The front part can be coupled to the rear part in many different ways. The end of the rear part can e.g. have a rounded shape and a front part with a corresponding rounded shape can be disposed thereon. It is also possible to combine segment-shaped front parts with corresponding recesses in the rear parts. However, the front parts are preferably substantially semi-circular bodies which are securely borne in corresponding recesses at the front end of the rear parts, wherein adjustment comprises a pivoting motion about the imaginary axis of rotation at the center of the circular shape. There are different possibilities of secure mounting without considerably interrupting the volume of the radiation-absorbing material, e.g. dove-tailed guidance means, guidance in grooves, retaining pins guided in slots, etc. The height of the rear part preferably substantially corresponds to the diameter of the semi-circular body, wherein the front ends of the rear part are displaced to the rear such that any required inclined position of the front edges of the collimator leaves is possible. This embodiment has the advantage that the pivoted front part also has the same height as the associated rear part for all possible positions. This is advantageous for the concrete design for bearing and guiding the collimator leaves.

The cross-sections of the collimator leaves preferably have asymmetrical trapezoidal shapes such that their side surfaces extend approximately parallel to the optical path, wherein the inner surfaces of the lateral sides bordering the outer collimator leaves extend at an inclination such that they join with the outer collimator leaves without leaving gaps. In this fashion, a half shadow is prevented since all limitations of the collimator opening correspond approximately to the optical path. As was mentioned above, such an embodiment of the collimator in accordance with the invention is very advantageous. The front parts preferably have sufficient lateral play to guarantee adjustment, despite the trapezoidal shape.

One embodiment provides that the collimator leaves can be displaced beyond the central line of the possible collimator opening to permit reproduction of tumors having any irregular contour, e.g. including U-shaped contours which require that the collimator leaves cross the central line of the collimator opening. This embodiment also facilitates modulation of the intensity of the rays through temporary covering of certain regions. A further advantage is that the collimator leaves can be closed asymmetrically, e.g. like a zipper. This considerably reduces leakage of rays in the closing region compared to that associated with closing all collimator leaves in the center. Clearly, to achieve such displacement beyond the central line, the length and distance of displacement of the collimator leaves must be dimensioned correspondingly.

In order to position the collimator leaves (like in the above-mentioned EP 0 245 768 B1 and in the largely identical EP 0 387 921 A1) a drive mechanism may be provided which adjusts several collimator leaves, one after the other. It is, however, preferred to provide each collimator leaf with one single controllable drive to permit quick computer-controlled shape changes. This is particularly important for dynamic irradiation of a tumor, wherein irradiation is enabled from different sides with relatively frequent changes. Even if the object of irradiation has an irregular shape and rapid change of the contour is required, maximum protection of the surrounding tissue is thereby ensured. The individual drives are also suitable if collimator leaves must be temporarily moved into the collimator opening during irradiation to weaken the intensity of radiation in certain regions. To increase the safety and reduce the number of drives, these individual drives preferably exhibit the forced coupling mentioned above.

Control of the collimator during operation thereof is preferably effected by a computer which adjusts the contour and position of the collimator opening to the object of irradiation in the respective direction of radiation, wherein the computer receives the data from a device for detecting the shape of the object of radiation and a control means examines the result of the adjustment. The collimator leaves can thereby be advantageously disposed in a displaceable collimator block which is provided for positioning the collimator opening relative to the object of irradiation and to the radiation source. The collimator block can be divided along a central line which permits separate displacement of these halves. Moving apart of the two halves additionally increases the collimator opening. The collimator block can also be mounted to a gantry which permits a relative motion between the collimator and the patient such that the patient can be irradiated from all sides through adjustment of the collimator opening to the shape of the object of irradiation. In this fashion, the collimator can be used to encircle a tumor to be irradiated, wherein this motion must not necessarily be circular but can also extend through three dimensions. A radiation method of this type is known, but is facilitated in combination with the invention since the inventive collimator provides improved construction and drive and the computing effort is considerably reduced. This method offers, in particular, high safety with regard to malfunction due to the forced coupling between the two drives.

The forced coupling of the drive of the rear parts of the collimator leaves and the actuator for the front parts can be realized by a transmission. To increase the space for the transmissions, the transmissions, optionally also the drives, can be disposed alternately at the top of one collimator leaf and at the bottom of the neighboring collimator leaf. This is particularly important if the collimator leaves must be very narrow, as is required for an exact reproduction of the shape of the tumor. A first embodiment of the drives provides that the actuator for the front parts is designed to align the front parts with respect to the radiation source when individual collimator leaves are adjusted, when all leaves are adjusted, or when some of the collimator leaves are adjusted. This permits movement of the overall collimator block or, through adjustment of the collimator block halves, to move them apart and thereby increase the collimator opening. This permits treatment of larger irradiation objects with a relatively small collimator without having to do without the inventive alignment of the front edges of the collimator leaves.

As drive, the rear part can have an associated collimator toothed rack into which a driving toothed wheel engages, wherein the collimator toothed rack associated with the rear part can also be embodied as teeth in a longitudinal edge of the rear part of the collimator leaves.

To provide good guidance of the collimator leaves, a rear section proximate the region of the gearing in the longitudinal edge of the rear part can be disposed in the collimator block at a displaced height such that a guiding element connected to the side of the collimator block above the gearing can engage in a guiding groove of the rear part or in the rear section. This produces secure guidance directly in the vicinity of the engagement region of the toothed wheel to provide exact play-free displacement of the collimator leaves. Clearly, additional guidance means can also be provided, e.g. a guidance for the edge of the rear part opposite to the gearing. In a particularly advantageous fashion, a guiding element is provided which is guided in a groove of the longitudinal edge of the rear part for securely retaining the collimator leaf in its position even if the neighboring collimator leaf assumes a substantially different position and is therefore no longer directly adjacent.

The driving means for adjusting the front part may be a front edge toothed rack which is hinged to the front part outside of its axis of rotation and into which a toothed gear engages to produce an adjustment path which differs from that of the rear part. The differing adjustment path permits corresponding adjustment of the front edge. Although this can be effected e.g. with separate drives, a forced mechanical coupling is preferred.

One embodiment of simple construction and reliable function provides that the collimator toothed rack and the front edge toothed rack are disposed on a longitudinal edge of the rear part and have different subdivisions to produce the differing adjustment paths, wherein a toothed wheel engages both toothed racks, wherein the subdivision difference lies within the tolerance limits of the gearing. With respect to a transmission disposed below a collimator, the subdivisioning of the front edge toothed rack is larger than that of the collimator toothed rack. With respect to a transmission disposed above a collimator, the subdivisioning of the front edge toothed rack must be smaller than that of the collimator toothed rack. This embodiment has, of course, only exemplary character and further possibilities are feasible, e.g. spindle drives with different pitches.

The driving toothed wheels or further toothed wheels which engage both toothed racks can be disposed in the collimator block. Alternatively, the further toothed wheels can be borne by the base frame. One toothed wheel can take over both functions or two separate toothed wheels can be provided.

In a further development, the driving toothed wheel engages in a driving toothed rack and is disposed in a displaceable collimator block or in two displaceable collimator block halves, and one further toothed wheel, which engages the collimator toothed rack and the front edge toothed rack, is disposed on a base frame. The collimator block as a whole or the collimator block halves—one for each part of the collimator leaves—can be displaced on the base frame. The base frame can thereby be disposed between the collimator block and the gantry or the base frame can be the gantry itself. The driving toothed rack can be a separate toothed rack or a continuation of the collimator toothed rack relative to a shorter front edge toothed rack. This embodiment has the advantage that even when displacing the collimator block or the collimator halves, any setting of the front edges of the collimator leaves with respect to the radiation source, once adjusted, is maintained so that the front edges are always aligned parallel to the radiation even if the collimator block or the collimator block halves are adjusted. This is effected by the further toothed wheel which engages both toothed racks thereby ensuring the relative orientation and positioning of both toothed racks throughout the entire travel region to considerably increase the possible adjustment region and the collimator opening.

Of course, there are many further possible types of control and forced mechanical couplings. The drive for the rear parts can e.g. be connected to a link drive for the adjustment of the front parts. These link drives can have different designs. A connecting link guide can be directly connected to the bearing of the driving toothed wheel and a slider of the connecting link guide can cooperate with the front part. The connecting link guides can also be directly connected to a base frame and displaceable collimator block halves—one for each part of the collimator leaves—are directly connected to the bearings of the driving toothed wheels. A concrete embodiment of a connecting link guide provides that a slider is mounted to a cable control which is guided to the front part and is mounted with one end above, and with the other end below the imaginary axis of rotation of the front part. A further possible embodiment consists in that the slider is mounted at a rear end of a two-armed lever wherein the axis of rotation of the lever is disposed on the rear part and its front end engages in the rear region of the front part to effect adjustment.

Preferably, a guidance is provided on at least one, preferably both longitudinal edges of each rear part which can be designed e.g. such that a groove is formed on the longitudinal edge in which a guiding element of the collimator block slides. Further possible guidance means are feasible to ensure that a collimator leaf is securely guided even when the neighboring collimator leaf is displaced to such an extent that the collimator leaf is exposed.

The collimator leaves can serve as compensating means for generating different radiation intensities by temporarily introducing them into the collimator opening during irradiation. This reduces the need for separate compensating means without excluding use thereof along with the inventive collimator.

The problems on which the invention is based, and embodiments of the invention are described below with reference to schematic drawings.

DESCRIPTION OF THE PREFERRED EMBODIMENT

Figure 1:
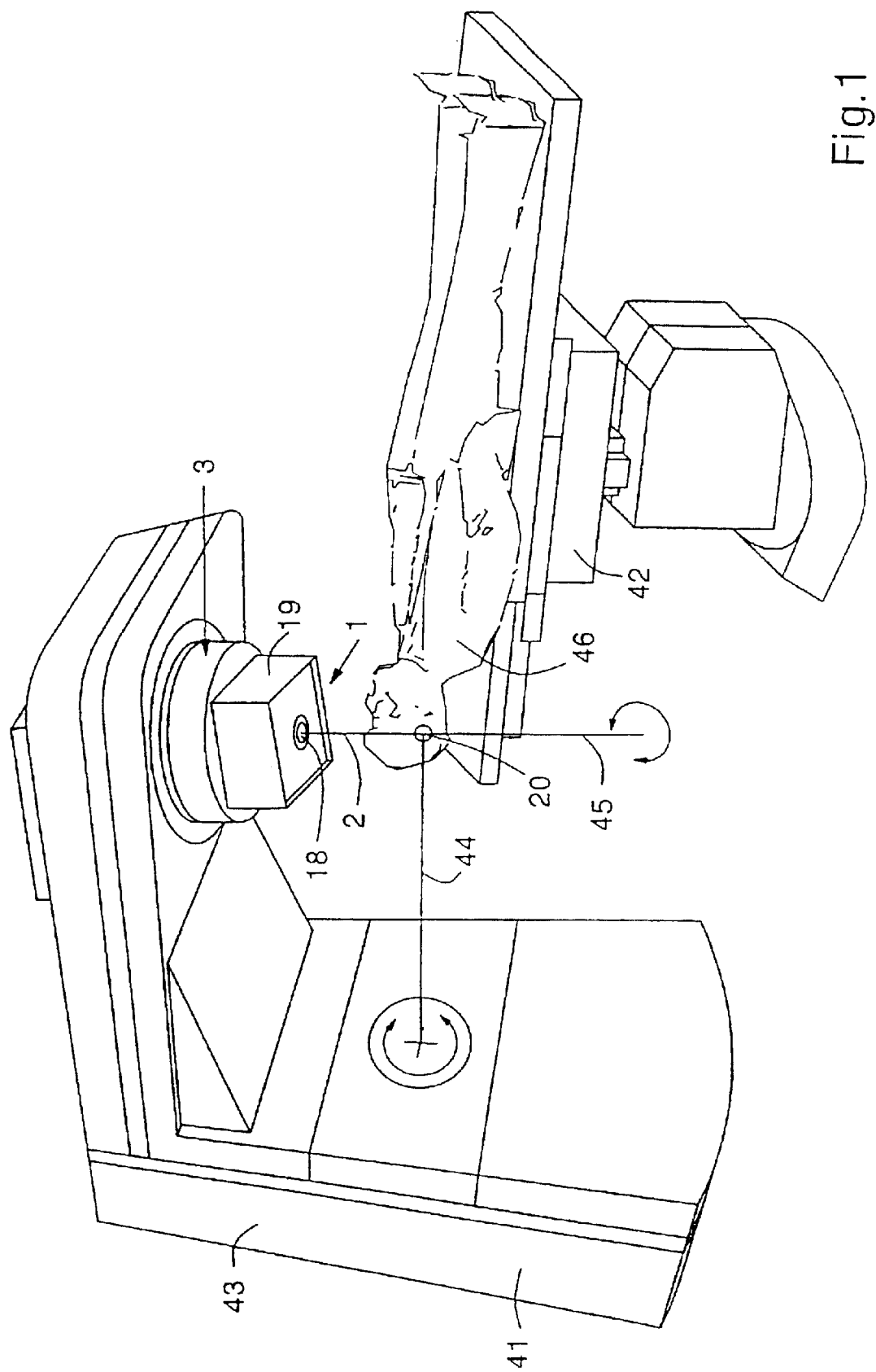
FIG. 1 shows the basic construction of a radiation device in which the inventive collimator can be used.

FIG. 1 shows the basic design of a radiation device in which the collimator 1 in accordance with the invention can be used. The collimator 1 is disposed on a collimator block 19 which is mounted to a gantry 41. The gantry 41 contains the radiation source 3. The radiation can be produced e.g. by a linear accelerator 43. The gantry 41 can be rotated about a horizontal axis of rotation 44, wherein the rays 2 are directed towards a radiation object 20, e.g. a tumor. The radiation object 20 is located in the isocenter of the rays 2, and the radiation source 3 as well as the collimator 1 circle around the patient 46 through rotation of the gantry 41. The treatment table 42 can also simultaneously rotate about a rotational axis 45 to further change irradiation of rays 2 onto the treatment object 20 within the patient 46. Of course, further adjustments are feasible. The intent is that the object to be treated 20 experiences maximum radiation dose by changing the different radiation directions while, however, protecting surrounding tissue to the greatest extent possible by only exposing it to the rays 2 for short periods of time. Furthermore, certain regions of the body must often be completely avoided such as e.g. the spinal cord or organs, wherein the irradiation directions must be chosen accordingly. The rays 2 are formed by the collimator opening 18 such that they impinge on the radiation object 20 in correspondence with its shape to protect the surrounding tissue. The profile of the tumor is detected e.g. through computer tomography recordings. This data is processed to generate a collimator opening 18 corresponding to this shape and can optionally irradiate different portions of the irradiation object 20 with different intensities. The shape and intensity are calculated and adjusted for each irradiation direction.

Figure 2:
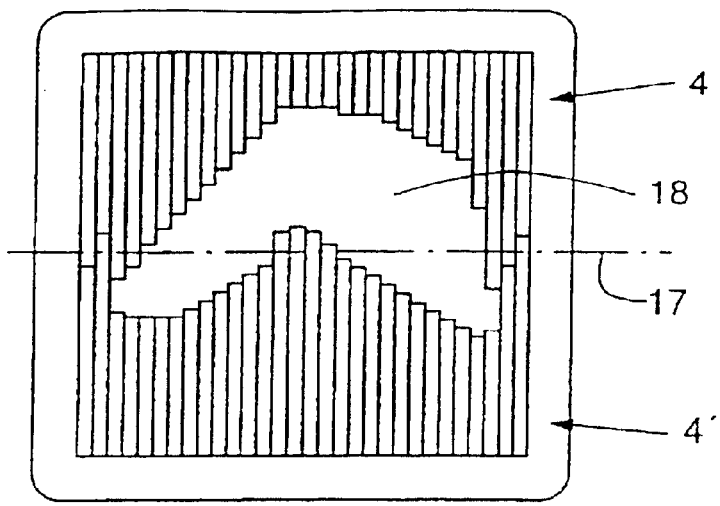
FIG. 2 shows a collimator opening of a multi-leaf collimator.

FIG. 2 shows a collimator opening 18 of a multi-leaf collimator. The invention concerns such a collimator 1 having the above-mentioned improvements which are also shown and explained in the subsequent figures. In accordance with the invention, the collimator leaves 4 and 4' can produce a collimator opening 18 which corresponds to the shape of the object to be treated 20 without producing a half shadow 47. This will be further explained below. FIG. 2 shows the principle of a collimator 1 designed as a multi-leaf collimator which reproduces the shape of a tumor in a collimator opening 18 using collimator leaves 4, 4'. Advantageous embodiments of the invention thereby provide that the collimator leaves 4 and 4' can be pushed beyond the central line 17 of the maximum possible collimator opening 18. This is required e.g. if the radiation object 20 has a U- or similar shape which can be reproduced only if the collimator leaves 4 and 4' extend beyond the central line 17. Moreover, the collimator leaves 4 and 4 can be closed, as shown at the left and right sides. The collimator leaves on these sides do not abut at the central line 17 but are staggered to reduce leakage radiation in this region.

Figures 3A, 3B:
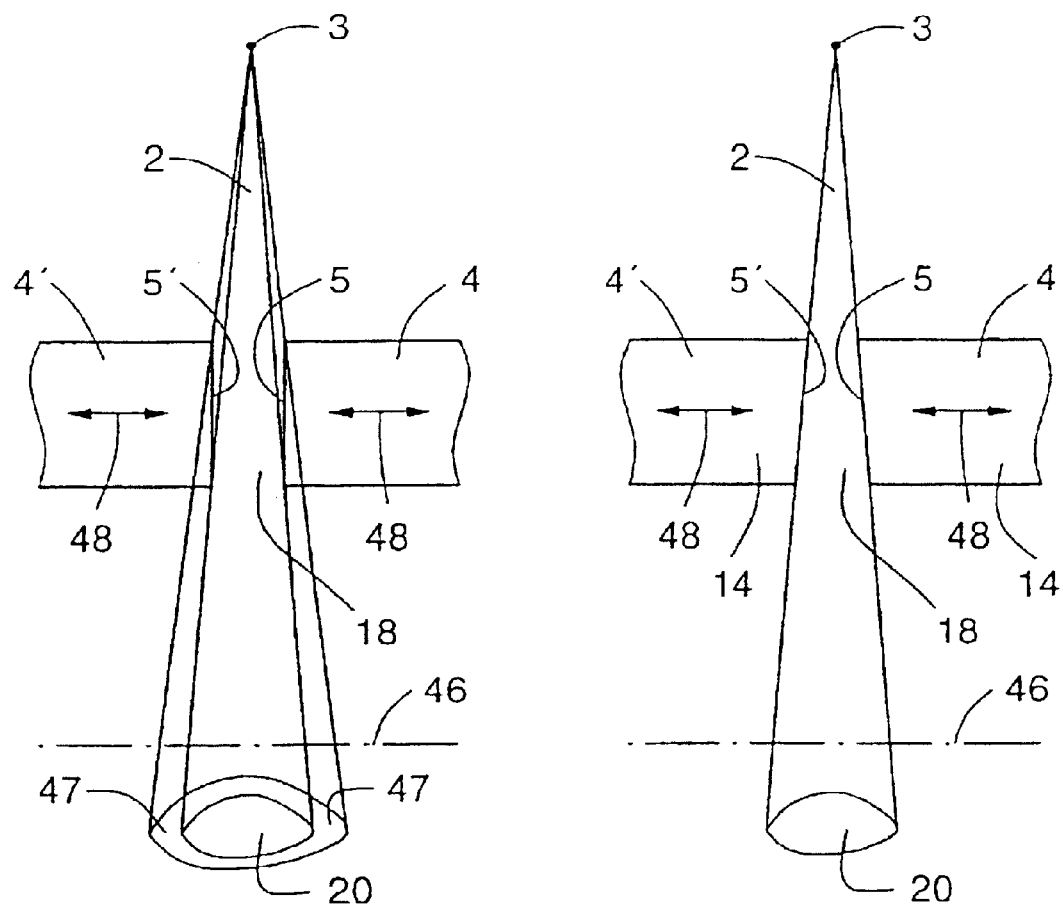
FIG. 3a shows the principle of half shadow production with collimators according to prior art.
FIG. 3b shows the principle of half shadow prevention by the inventive collimator.

FIG. 3a shows the principle of half shadow 47 production in some collimators of prior art. The collimator leaves 4 and 4 therein have straight front edges 5 and 5'. If rays 2 from a substantially point-like radiation source 3 pass through the collimator opening 18, part of these rays 2 must pass through the entire material thickness and another part of the rays does not contact the material. In the intermediate region, the rays penetrate only part of the material of the collimator leaves 4, 4' and are partly absorbed to produce half shadows 47. The further the collimator leaves 4 and 4' are moved apart by the adjustment 48, the larger this half shadow 47. Due to this half shadow 47, the surroundings of this radiation object 20 are also irradiated with attenuated intensities 2, in addition to the irradiation object 20. This causes unnecessary damage to the surrounding tissue of the patient 46. With rounded front edges 5, 5' or with collimator leaves 4, 4' which are disposed on top of one another in steps, such half shadows can be reduced, however, not eliminated.

FIG. 3b shows the principle of avoiding half shadows 47 in the inventive collimator 1. The inventive collimator leaves 4 and 4' are designed such that their front edges 5 and 5' are always oriented in parallel to the rays 2, despite their linear displacement to thereby ensure that a ray 2 either completely passes through the collimator opening 18 and hits the radiation object 20 or is absorbed by the entire material thickness of the collimator leaves 4 and 4'. The front edges 5 and 5' are aligned according to the adjustment 48 of the collimator leaves 4 and 4' thereby ensuring that a half shadow 47 is prevented for all widths of the collimator opening 18.

Figure 3C:
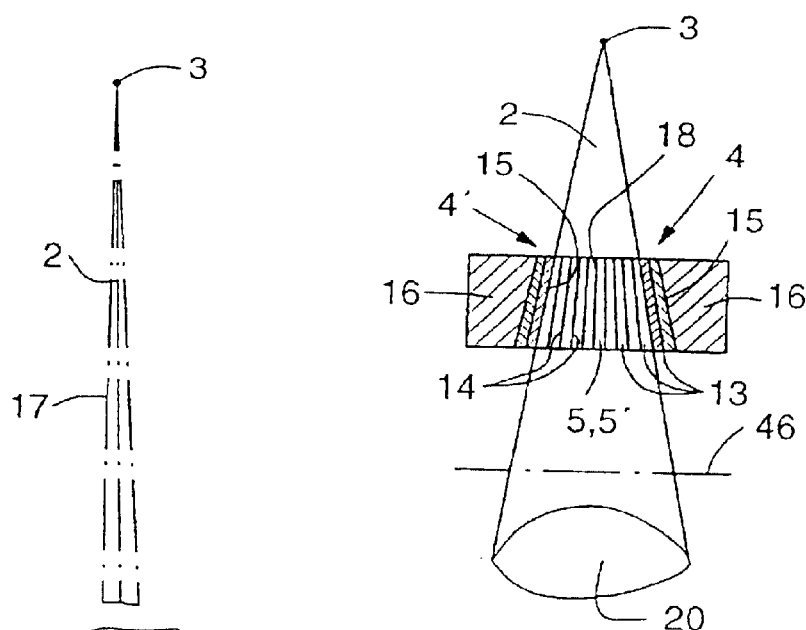
FIG. 3c shows partial prevention of half shadows through a trapezoidal embodiment of the collimator leaves.

FIG. 3c shows partial prevention of a half shadow by designing the collimator leaves 4 and 4' in an asymmetrical trapezoidal shape 13. The viewing direction of the collimator 1 is rotated through 90° with respect to the representations of FIGS. 3a and 3b and directed onto the front edges 5, 5'. The design shown prevents the side surfaces 14 of the collimator leaves 4, 4' and the lateral borders 16 from producing half shadows 47. The collimator leaves 4 and 4' thereby have an asymmetrical trapezoidal shape 13 such that the two side surfaces 14 of each collimator leaf 4, 4' extend parallel to the rays 2. The inner surfaces 15 of the lateral borders 16 also have a corresponding alignment and are adjacent to the side surfaces 14 of the outer collimator leaves 4 and 4', without leaving gaps.

In FIG. 3c the two outer collimator leaves 4 and 4' are shown in cross section, since they are closed. The other collimator leaves 4, 4' are opened to a greater or lesser degree to thereby form the collimator opening 18. A corresponding design of the collimator leaves 4, 4' was disclosed in prior art, but had the functional problems discussed above. Only the inventive design of the collimator leaves 4 and 4' permits guaranteed trouble-free function despite the asymmetrical trapezoidal shapes 13 without having to accept large tolerances or introduce a further set of collimator leaves, displaced by 90°, in the optical path 2. In this fashion, both the functions shown in FIG. 3b and FIG. 3c can be provided by the same set of collimator leaves 4 and 4'. This is a considerable advantage over prior art.

Figure 4:
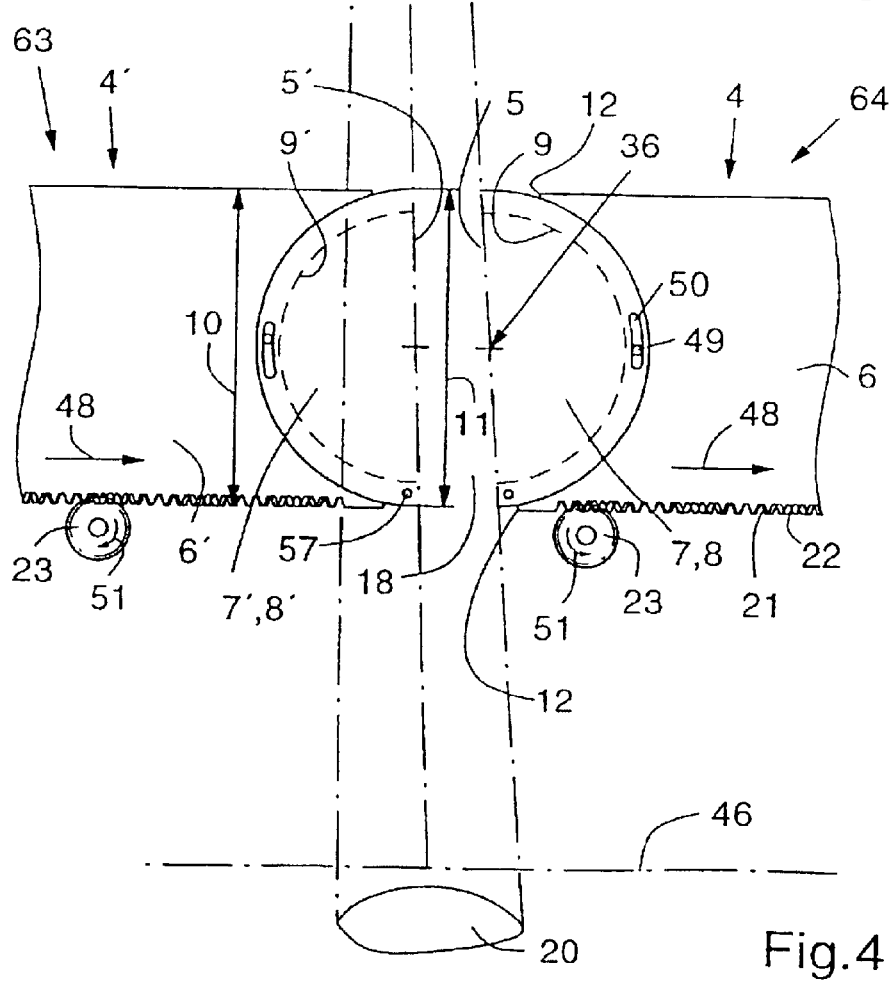
FIG. 4 shows the principle of an inventive embodiment.

FIG. 4 shows the principle of an inventive embodiment of the collimator 1. The collimator leaves 4 and 4' comprise rear parts 6 and 6' and front parts 7 and 7'. The latter are formed as semi-circular bodies 8 and 8' and are disposed in corresponding recesses 9 and 9' of the rear parts 6 and 6' of the collimator leaves 4 and 4'. Such mounting can e.g. be effected when the front parts 7 and 7' have a groove 56 about their semi-circular shape into which the rear parts 6 and 6' engage with corresponding graduation in the region of the corresponding recesses 9 and 9' such that full material thickness is maintained. Retaining pins 49 are provided within corresponding slots 50 for securely mounting the front parts 7 and 7'. The length of the slots 50 defines the adjustment region. When the collimator leaves 4 and 4' are displaced in accordance with the arrows 48, the front parts 7 and 7' are simultaneously turned about an imaginary axis of rotation 36 such that the front edges 5 and 5' are always aligned parallel to the rays 2. This means that the front edges 5 and 5' are perpendicular in the region of the central line 17 of the possible collimator opening 18 and, when displaced from this central line 17, are oriented in the one or the other direction such that they point towards the radiation source 3. To guarantee these adjustments, the front ends 12 of the rear parts 6 and 6' must be set back correspondingly such that the front edges 5 and 5' are located in the region of these front ends 12 only when maximum adjustment has been reached. The height 12 of the rear parts 6 and 6' is preferably as large as the diameter 11 of the semi-circular bodies 8 and 8', thereby ensuring constant material thickness. This embodiment has the further advantage that the front parts 7 and 7' always have the same height as the rear parts 6 and 6'.

FIG. 4 also shows a transmission for the collimator leaves 4 and 4' which ensures that the front edges 5 and 5' are correctly aligned for each position of the collimator leaves 4 and 4'. This can be effected through forced mechanical coupling defined by a driving toothed wheel 23 which engages a collimator toothed rack 21 as well as a front edge toothed rack 22, wherein these toothed racks 21 and 22 have different subdivisions 52, 53 or 54 (see FIGS. 5a and b) to achieve the different required adjusting motions. It must thereby be guaranteed that the different subdivisions 52,53 or 54 lie within the tolerance limits of the gearing of the driving toothed wheel 23 to prevent jamming. The arrow 51 shows the direction of rotation of the driving toothed wheels 23 and the arrows 48 show the adjustment of the collimator leaves 4 and 4' caused by this driving direction. The collimator leaf 4 of FIG. 4 assumes the maximum opening position 64 and the collimator leaf 4 assumes the maximum over-travel 63. The latter represents maximum traverse of the central line 17. This over-travel permits the collimator opening 18 to reproduce a tumor 20 of any shape, up to the size of the maximum collimator opening 18.

The arrangement of the drives in FIG. 4 at the lower end of the collimator leaves 4 and 4 is merely an example. It is also possible to dispose these drives 23,21,22 in the upper region or alternately at the bottom of a collimator leaf 4 or 4' and at the top of the neighboring collimator leaf 4 or 4' to thereby obtain more space for the drives. In the embodiment of FIG. 4, the teeth of the collimator toothed rack 21 are milled into a longitudinal edge 37 (see FIG. 7) of a rear part 6 or 6'. The front edge toothed rack 22 is disposed within a central groove 66 of this milled collimator toothed rack 21 (FIG. 8) and is pivotally connected to the front part 7,7' via a pivot 57 to effect adjustment. Since the collimator toothed rack 21 and the front edge toothed rack 22 have different divisions 52,53,54, the driving toothed wheel 23 provides different advances. The advance difference can be defined by the subdivision differences.

Figure 5A:
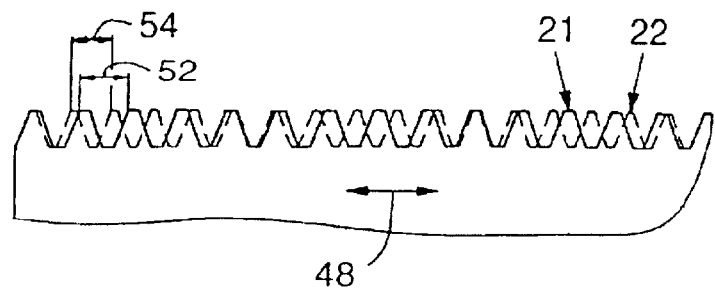
FIG. 5a shows tooth subdivisions in a first configuration.
Figure 5B:
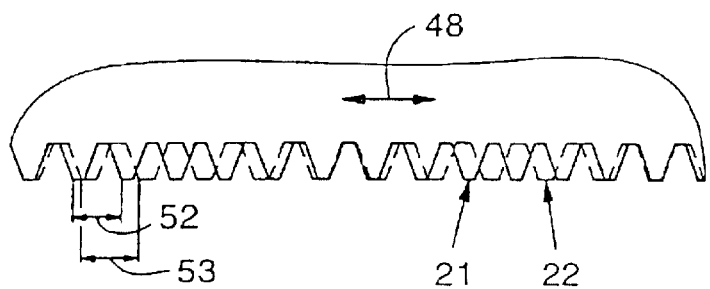
FIG. 5b shows tooth subdivisions in a second configuration.

The different tooth subdivisions 52,53,54 are shown in FIGS. 5a and 5b. FIG. 5a shows the subdivisions 52,54 of collimator toothed rack 21 and front edge toothed rack 22 when they are disposed above the collimator leaves 4 and 4'. In this case, the subdivision 52 of the collimator toothed rack 21 is larger than the subdivision 54 of the front edge toothed rack 22 which produces a larger advance of the collimator toothed rack 21 compared to that of the front edge toothed rack 22. If the rear part 6, 6' is moved in the direction of the double arrow 48, its displacement is somewhat larger than that of an upwardly disposed front edge toothed rack 22 to turn the front part 7,7' such that the front edge 5, 5' extends parallel to the rays 2. This alignment is ensured in all positions, even when the central line 17 is crossed. In FIG. 5b, the subdivision 52 of the collimator toothed rack 21 is smaller than the subdivision 53 of the front edge toothed rack 22 when it is disposed below the collimator leaves 4 and 4'. The function is the same as described above with the difference that, in this arrangement, the advance of the front edge toothed rack 22 must be larger than that of the collimator toothed rack 21 for corresponding alignment of the front edges 5 and 5'.

Of course, other arrangements are also possible. The toothed racks 21 and 22 can also be disposed on rear extensions of the collimator leaves 4 or 4 and it is also possible to provide a separate driving toothed wheel 23 to guarantee allocation of the advances for the two toothed racks 21 and 22 via a no-load toothed wheel 24.

Figure 6:
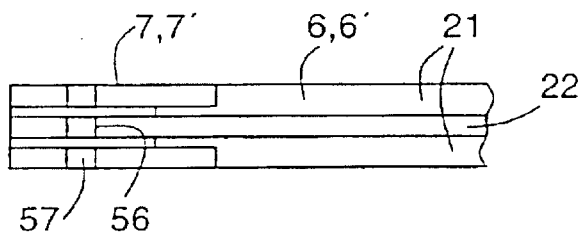
FIG. 6 shows coupling of a front part of a collimator leaf.

FIG. 6 shows coupling of a front part 7 or 7' to a rear part 6 or 6' of a collimator leaf 4 or 4' and shows how the front edge toothed rack 22 is guided in a groove 66 which was milled in the center of the collimator toothed rack 21. Both gearings are therefore at the same height and a single toothed wheel 23 or 24 can engage both gearings. Since the collimator toothed rack 21 is directly milled in a longitudinal edge 37 of a rear part 6 or 6', this adjustment will be transferred directly onto this rear part 6 or 6'. To adjust the front parts 7 and 7', the front edge toothed rack 22 is pivotally mounted 57 to the front part 7 or 7' for transmitting the adjustment motion.

Figure 7:
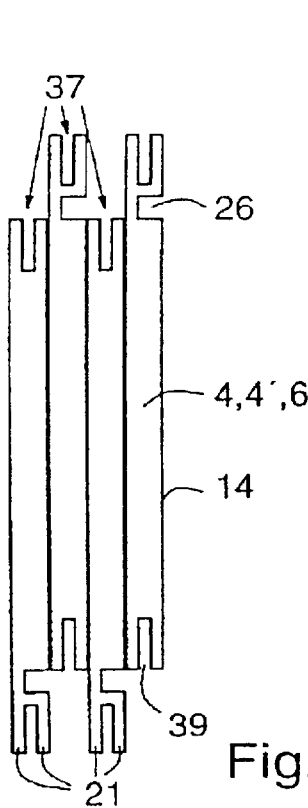
FIG. 7 shows an arrangement of collimator leaves.

FIG. 7 shows displaced arrangement of the rear parts 6 or 6' of the collimator leaves 4 or 4'. This displaced arrangement serves to accommodate guidance means 38 via grooves 26 and 39. Such grooves 26, 39 can be milled into either the side surfaces 14 or into the longitudinal edges 37.

Figure 8:
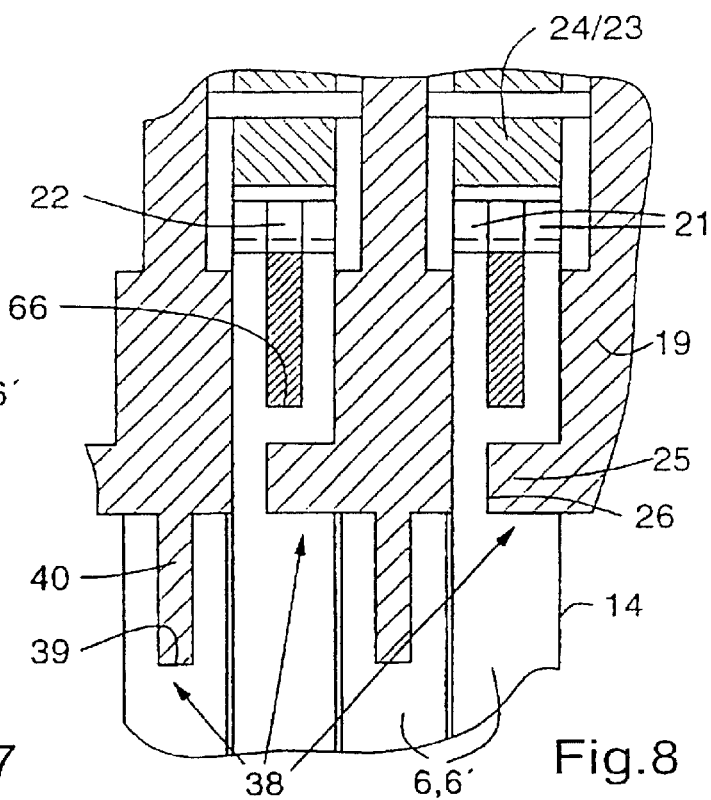
FIG. 8 shows mounting of collimator leaves.

FIG. 8 shows the arrangement of such guidance means 38 as well as disposition of a driving toothed wheel 23, a toothed wheel 24, the collimator toothed rack 21, and the front edge toothed rack 22. A first guidance 38 is defined by a groove 39 milled into the longitudinal edge 37 of the rear part 6 or 6' in which a guiding element 40 of the collimator block 19 runs. A further guidance 38 has a guiding groove 26 located in the side surface 14 of a rear part 6 or 6'. A guiding element 25 of the collimator block 19 also engages in this guiding groove 26. The guiding groove 26 is disposed at the end of the rear part 6 or 6' where the collimator toothed rack 21 is located. The collimator toothed rack 21 is milled into a longitudinal edge 37 of the rear part 6 or 6'. The central region of this collimator toothed rack 21 is provided with a groove 66 in which the front edge toothed rack 22 is disposed such that a toothed wheel 24 or 23 engages in said gearing and also in the gearing of the collimator toothed rack 21. Different advances are achieved due to the different subdivisions, as described above.

Figure 9A:
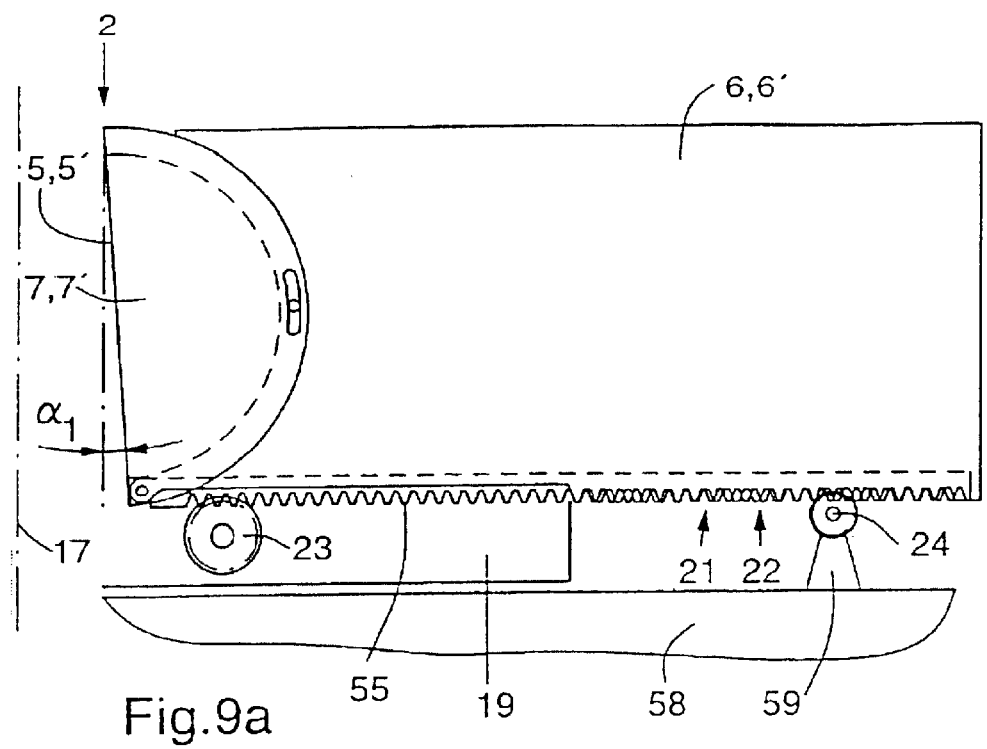
FIG. 9a shows a first positioning of a second embodiment.
Figure 9B:
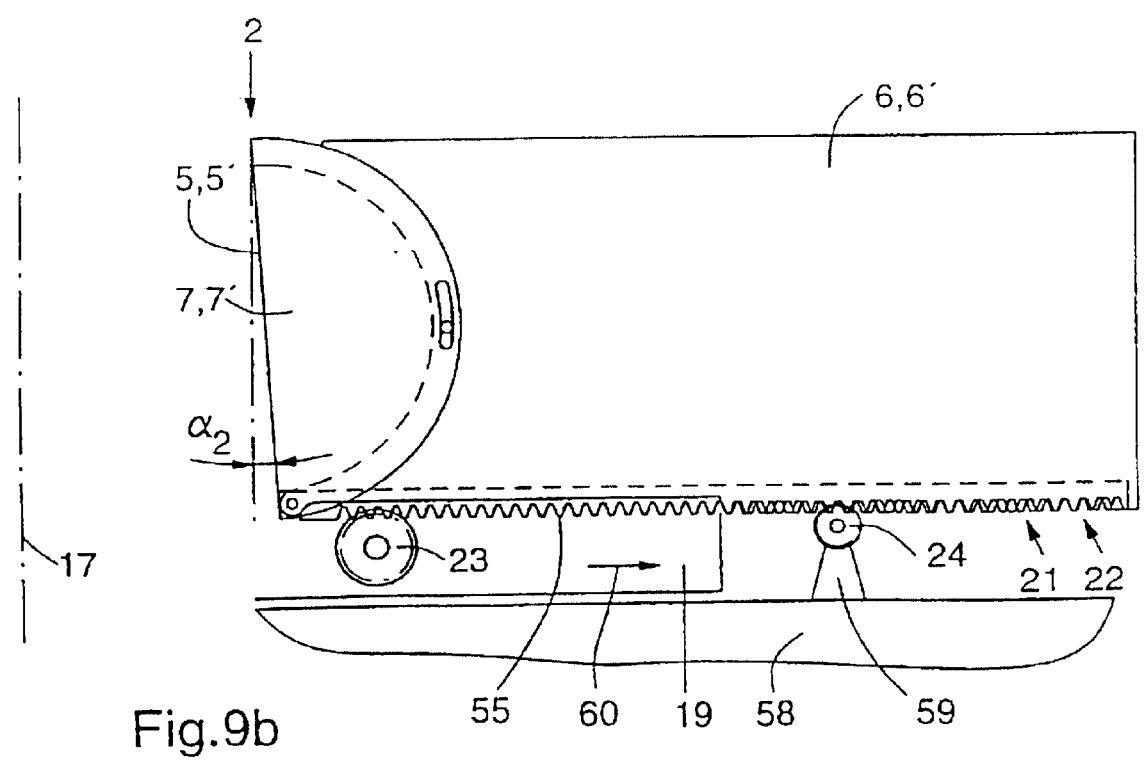
FIG. 9b shows a second positioning of the second embodiment.

FIGS. 9a and 9b show a second embodiment of the invention which differs from the first embodiment in that a driving toothed rack 55 and a driving toothed gear 23 are located in the front region of the rear part 6 or 6' and the collimator toothed rack 21 and the front edge toothed rack 22 are disposed in the rear region. A non-loaded toothed wheel 24 engages both toothed racks 21 and 22 to transmit the differing advance to the front edge toothed rack 22. In the present embodiment, the driving toothed wheel 23 is disposed in a collimator block 19 or in a collimator block half which can be displaced with respect to a base frame 58. The further toothed wheel 24 is connected to the base frame 58 via a bearing 59. In this arrangement, the front edges 5 and 5', once correctly adjusted, remain aligned and parallel to the rays 2 even when the entire collimator block 19 is displaced with respect to the radiation source 3 or if two collimator block halves are moved apart to enlarge the collimator opening. This is shown in FIGS. 9a and 9b. The collimator block 19 of FIG. 9a is in a first position with respect to the center line 17 and, in FIG. 9b, in a second position displaced in the direction of the arrow 60. This displacement produced a change in the angle $\alpha_2$ of the front part 7 or 7' via the mechanics shown, such that the front edges 5 or 5' also extend parallel to the rays 2 in the new position. The figure shows that the front edge 5 or 5' in FIG. 9b has a larger distance from the center line 17 than in FIG. 9a, and the angle $\alpha_1$ was increased to $\alpha_2$ through displacement.

The driving toothed rack 55 in the front region can thereby be identical to the gearing of the collimator toothed rack 21 or have a different subdivision or tooth size. In any event, the front edge toothed rack 22 must not have any teeth in this region and lies in the groove 66 at a depth which permits the driving toothed wheel 23 to run in the driving toothed rack 55 and the front edge toothed rack 22 to be freely displaced in this region.

Figure 10A:
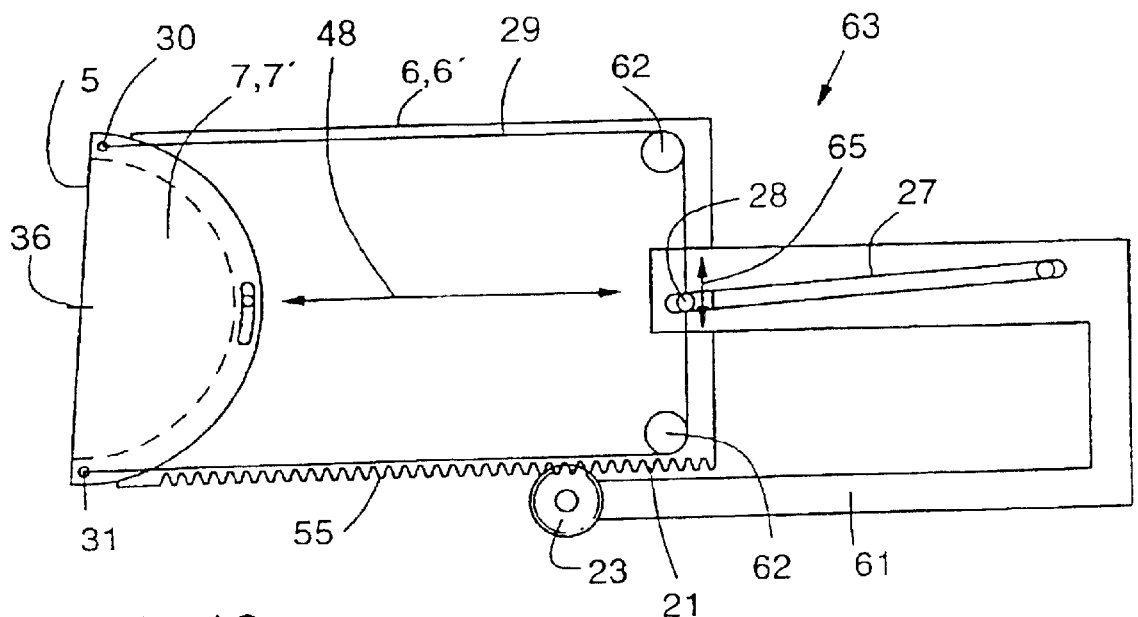
FIG. 10a shows a first positioning of a third embodiment.
Figure 10B:
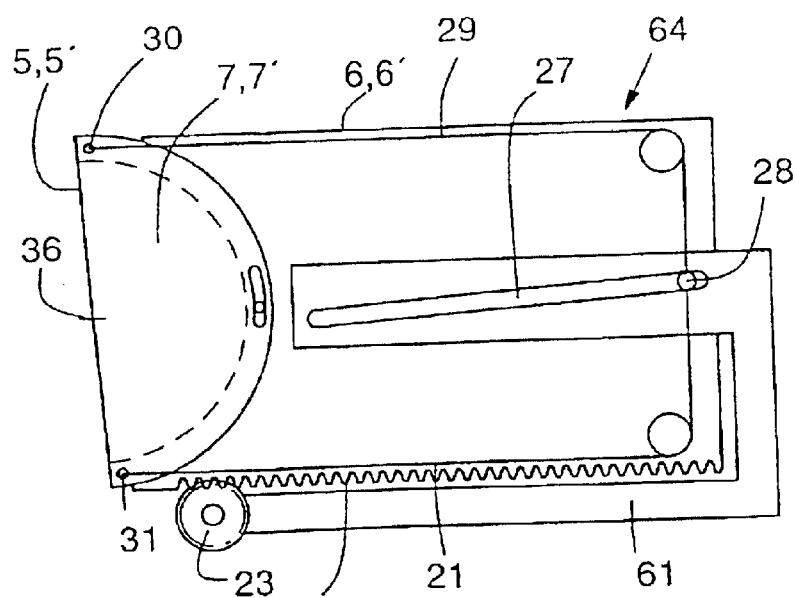
FIG. 10b shows a second positioning of the third embodiment.

FIGS. 10a and 10b show a third embodiment wherein the adjusting motion of the front parts 7 and 7' is effected through a linkage. In this embodiment as well, the rear parts 6 or 6' are provided with a driving toothed rack 55 for adjusting the rear part 6 or 6' via a driving toothed wheel 23. A connecting link guide 27 is joined by a rigid connection 61 to the driving toothed wheel 23 for producing adjustment of the front part 7 or 7'. A slider 28 runs in this connecting link guide 27 which is mounted to a cable drive 29. One end 30 of this cable drive 29 is mounted above the imaginary axis of rotation 36 at the front part 7 or 7' and the other end 31 below said imaginary axis of rotation 36.

FIGS. 10a and 10b show the possible adjustment range. FIG. 10a shows the position of the maximum over-travel 63 and FIG. 10b shows the maximum opening 64. The adjustment displacement 48 is transferred via the driving toothed wheel 23 to the rear part 6 or 6' and the slider 28 is displaced by the connecting link guide 27 in the direction of the arrow 65.

Figure 11:
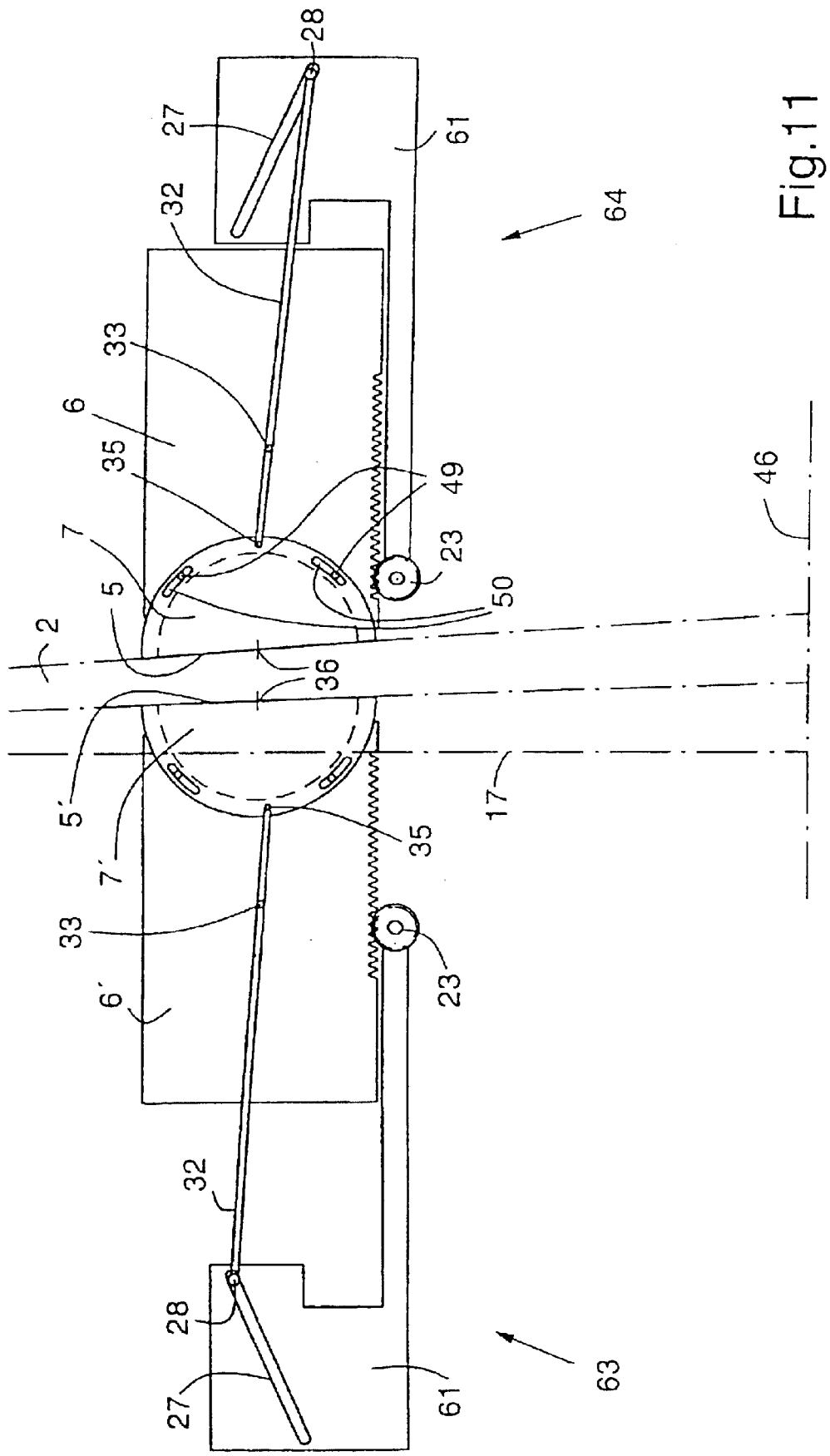
FIG. 11 shows a fourth embodiment.

FIG. 11 shows a fourth embodiment which differs from the third embodiment in that the slider 28 is located at the end of a two-armed lever 32. The lever 32 pivots on the rear part 6 or 6' via a rotation axle 33. The front end 35 of the two-armed lever 32 pivots on the front part 7 or 7', i.e. in the rear region, removed from the imaginary axis of rotation 36.

In this embodiment, the two-armed lever 32 is pivoted by the connecting link guide 27 thereby effecting the adjustment leading to the corresponding alignment of the front edges 5 or 5' of the collimator leaves 4 or 4'. A certain recess must be provided in the rear parts 6 or 6' for accommodating the two-armed lever 32. FIG. 11 shows the maximum over-travel 63 on one side and the maximum opening 64 on the other side.

Figure 12:
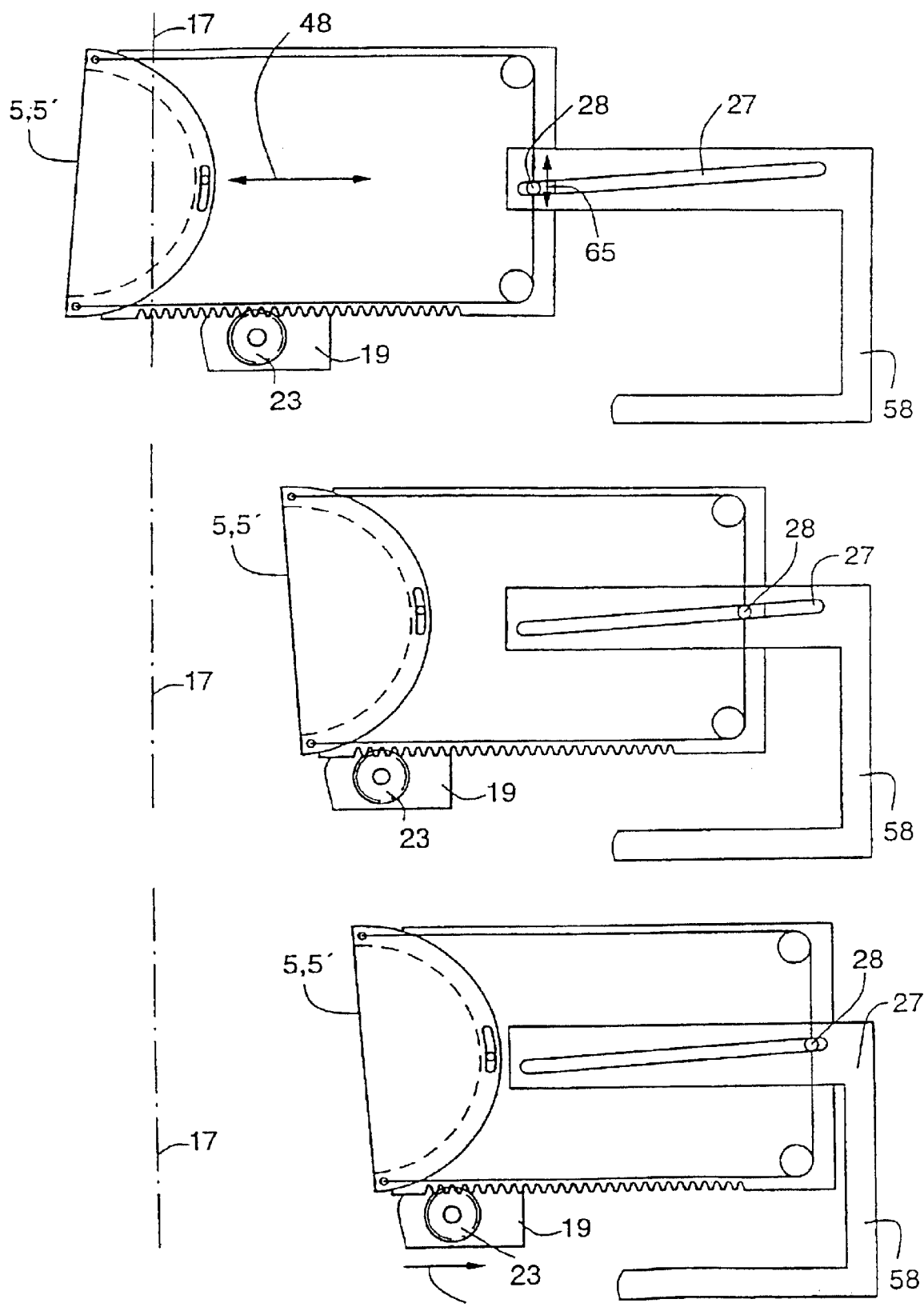
FIG. 12 shows a further design of the second embodiment.

FIG. 12 shows a further embodiment which is a variation of FIGS. 10a and b. It differs in that the connecting link guides 27 are connected to the base frame 58 and the driving toothed wheels 23 are connected to the collimator block 19 or collimator block halves. In this fashion, the collimator opening 18 can also be enlarged. The connecting link guides 27 must have a length which corresponds to the entire adjustment distance, i.e. the adjustment distance of the collimator leaves 4,4' and the adjustment distance of the collimator block halves. The embodiment of FIG. 11 can be modified accordingly.

The embodiments shown are, of course, only exemplary. Further embodiments are feasible in particular with respect to the forced coupling, and also with respect to the drives and design of the two parts of the collimator leaves.

List of reference numerals

1 collimator
2 rays
3 radiation source
4,4' collimator leaves
5,5' front edges of the collimator leaves
6,6' rear part of the collimator leaves
7,7' front part of the collimator leaves
8,8' semi-circular body
9,9' corresponding recesses
10 height of the rear part
11 diameter of the semi-circular body
12 front ends of the rear part
13 asymmetrical trapezoidal shape
14 side surfaces of the collimator leaves
15 inner surfaces of the lateral borders
16 lateral borders of the possible collimator opening
17 central line of the possible collimator opening
18 collimator opening
19 collimator block
20 radiation object (tumor)
21 collimator toothed rack
22 front edge toothed rack
23 driving toothed wheel
24 toothed wheel
25 guiding element
26 guiding groove 27 connecting link guide
28 slider
29 cable control
30 end of the cable control
31 other end of the cable control
32 two-armed lever
33 rotation axle of the two-armed lever
34 rear end of the two-armed lever
35 front end of the two-armed lever
36 imaginary axis of rotation
37 longitudinal edge of the rear part
38 guidance
39 groove
40 guiding element
41 gantry
42 treatment table
43 linear accelerator
44 horizontal axis of rotation of gantry
45 axis of rotation of treatment table
46 patient
47 half shadow
48 arrow: adjusting motion of the collimator leaves
49 retaining pin
50 slot
51 arrow: direction of rotation of the driving toothed wheel
52 subdivision of the collimator toothed rack
53 subdivision of a front edge toothed rack disposed below a collimator
54 subdivision of a front edge toothed rack disposed above a collimator
55 driving toothed rack
56 groove for guiding the front part in a rear part
57 pivoting of the front edge toothed rack to the front part
58 base frame
59 pivoting of the further toothed wheel
60 arrow: displacement of the collimator block
61 fixed connection: connecting link guide—driving toothed wheel
62 deflecting rollers
63 maximum over-travel of a collimator leaf
64 maximum opening of a collimator leaf
65 arrow: adjustment of the slider 28
66 groove

What is claimed is:

1. A multiple blade collimator device for collimating a beam of high-energy radiation emanating from a substantially point-like radiation source for irradiation of a treatment object and for stereotactic conformation radio therapy of tumors, the collimator device containing a plurality of opposing collimator blades from radiation-absorbing material which can be positioned into an optical path of the radiation to define arbitrary collimator shapes, the collimator device comprising:
   rear blade parts;
   front blade parts, each front blade part being linked to one associated rear blade part to form one collimator blade and in such a fashion that substantially no gap is generated in a volume of the radiation-absorbing material, each front blade part having a front edge;
   means for linearly displacing each of said rear blade parts towards and away from a central axis of the radiation beam; and
   means for adjusting each of said front blade parts in dependence on a position of a respective rear blade part to which said front blade part is linked such that said front edge is always parallel to the optical path of the radiation.

2. The collimator device of claim 1, wherein at least one of said linear displacement means and said adjusting means comprise a forced mechanical coupling between all positions of said rear parts and of said respective front parts to align said front edges.

3. The collimator device of claim 2, wherein said forced coupling between said linear displacing means for said rear parts of said collimator blades and the adjusting means for said front parts is effected via transmissions.

4. The collimator device of claim 3, wherein said transmissions for said collimator blades are disposed alternately above, for one collimator blade, and below, for a neighboring collimator blade.

5. The collimator device of claim 3, wherein said adjusting mean for said front parts is designed to align said front edges with respect to the radiation source in response to an individual adjustment of said respective collimator blade as well as in response to an adjustment of at least some of said collimator blades.

6. The collimator device of claim 5, wherein said adjusting means comprise a link member.

7. The collimator of claim 6, wherein said link member comprises a connecting link guide rigidly cooperating with a bearing of a driving toothed wheel and a link guide slider cooperating with said front part.

8. The collimator of claim 7, further comprising a base frame and displaceable collimator block halves rigidly connected to the bearings of driving toothed wheels, wherein each block half accommodates one group of said collimator blades and wherein said connecting link guide is rigidly connected to said base frame.

9. The collimator of claim 7, further comprising a cable control mounted to said slider, guided towards said front part, and mounted at one end above an imaginary axis of rotation and at an other end below an imaginary axis of rotation of said front part.

10. The collimator device of claim 7, wherein said link member comprises a double-armed lever having a rear end to which said slider is mounted, wherein said lever is disposed with a rotation axle on said rear part and with a front end on a rear region of said front part.

11. The collimator device of claim 3, wherein said rear part has a collimator toothed rack into which a driving toothed gear engages.

12. The collimator device of claim 11, wherein said collimator toothed rack associated with said rear part is designed as gearing in a longitudinal edge of said rear part.

13. The collimator device of claim 12, further comprising a collimator block in which said collimator blades are disposed, wherein in a region of said gearing in said longitudinal edge, an adjacent rear part is vertically displaced in said collimator block such that, above said gearing, a guiding element which is connected to a side of said collimator block engages in a guiding groove of said rear part.

14. The collimator device of claim 11, wherein said adjusting means comprise a front edge toothed rack linked to said front part outside of an axis of rotation thereof into which a toothed wheel engages to effect an adjustment path for said front part which differs than an adjustment path of said rear part for aligning said front edge.

15. The collimator device of claim 14, wherein said collimator toothed rack and said front edge toothed rack are disposed at a longitudinal edge of said rear part and have different subdivisions for obtaining different adjustment paths, wherein a toothed wheel engages both toothed racks with a subdivision difference lying within gearing tolerance limits.

16. The collimator device of claim 15, wherein a subdivision of said front edge toothed rack, disposed below a collimator blade, is larger than a subdivision of said collimator toothed rack.

17. The collimator device of claim 15, wherein a subdivision of said front edge toothed rack, disposed above said collimator blade, is smaller than a subdivision of said collimator toothed rack.

18. The collimator device of claim 15, further comprising a collimator block in which said collimator blades are disposed and a base frame supporting said collimator block, wherein said toothed wheel is disposed in a displaceable collimator block and further comprising an additional toothed wheel engaging said collimator toothed rack and said front edge toothed rack and disposed on said base frame for displacing said collimator block relative to said base frame.

19. The collimator device of claim 14, further comprising a base frame in which said toothed wheel is disposed.

20. The collimator device or claim 14, further comprising a collimator block in which said collimator blades are disposed, wherein said toothed wheel is disposed in said collimator block to simultaneously serve as a driving toothed wheel.

21. The collimator device of claim 1, wherein said front parts are substantially semi-circular bodies which are securely disposed in corresponding recesses at a front end of said rear parts, wherein said adjusting means generate a pivoting motion about an imaginary axis of rotation lying in a circular center of said semi-circular body.

22. The collimator of claim 21, wherein a height of said rear part substantially corresponds to a diameter of said semi-circular body, wherein front ends of said rear parts are set back to allow all required inclined positions of said front edges of said front blade parts.

23. The collimator of claim 1, wherein cross-sections of said front parts and said rear parts have an asymmetrical trapezoidal shape such that side surfaces thereof extend approximately parallel to the optical path, and further comprising limitations within which the front and rear blade parts are mounted, wherein said limitations have inner surfaces bordering outer collimator blades which extend at an inclined angle to abut these outer collimator blades without leaving gaps.

24. The collimator device of claim 23, wherein said front parts have sufficient lateral play to permit adjustment, despite their trapezoidal shapes.

25. The collimator device of claim 1, wherein said front edges can be displaced beyond a center line of a possible collimator opening.

26. The collimator device of claim 1, wherein each collimator blade comprises an individual displacing means and an individual adjusting means each of which can be individually controlled.

27. The collimator device of claim 1, further comprising a computer communicating with at least one of said displacing means and said adjusting means to adjust a contour and position of a collimator opening with respect to the radiation object in a respective direction of radiation, wherein said computer obtains adjustment data from a device for detecting a shape of the radiation object and further comprising a control means to examine a result of said contour adjustment.

28. The collimator device of claim 1, further comprising a collimator block in which said collimator blades are disposed for positioning a collimator opening relative to the radiation object and the radiation source.

29. The collimator device of claim 28, further comprising a gantry on which said collimator block is disposed, said gantry effecting relative motion between said collimator block and a patient such that the patient can be exposed to radiation from all sides, wherein a collimator opening is adjusted to the shape of the radiation object.

30. The collimator of claim 1, wherein at least one longitudinal edge of said rear part has a guide.

31. The collimator of claim 30, further comprising a collimator block in which said collimator blades are disposed, wherein said guide is a groove in said longitudinal edge in which a guiding element, cooperating with or integral with said collimator block, slides.

32. The collimator of claim 1, wherein said displacing means function as compensating means for generating different radiation intensities via temporary insertion of collimator blades into a collimator opening during irradiation.

* * * * *